(12) United States Patent
Shima et al.

(10) Patent No.: US 7,612,230 B2
(45) Date of Patent: Nov. 3, 2009

(54) METHOD FOR PRODUCING ACRYLIC ACID

(75) Inventors: Masahide Shima, Kobe (JP); Tsukasa Takahashi, Himeji (JP)

(73) Assignee: Nippon Shokubai Co., Ltd., Osaka (JP)

( * ) Notice: Subject to any disclaimer, the term of this patent is extended or adjusted under 35 U.S.C. 154(b) by 0 days.

(21) Appl. No.: 10/585,793

(22) PCT Filed: Jan. 28, 2005

(86) PCT No.: PCT/JP2005/001627

§ 371 (c)(1),
(2), (4) Date: Jul. 12, 2006

(87) PCT Pub. No.: WO2005/073160

PCT Pub. Date: Aug. 11, 2005

(65) Prior Publication Data

US 2007/0129570 A1    Jun. 7, 2007

(30) Foreign Application Priority Data

Jan. 30, 2004    (JP) .............................. 2004-024181

(51) Int. Cl.
*C07C 51/235* (2006.01)
*C07C 57/055* (2006.01)

(52) U.S. Cl. .................. 562/535; 562/534; 562/532

(58) Field of Classification Search .................. None
See application file for complete search history.

(56) References Cited

U.S. PATENT DOCUMENTS

| | | | | |
|---|---|---|---|---|
| 2,558,520 A | * | 6/1951 | Hoyt et al. .................. | 568/486 |
| 4,871,700 A | * | 10/1989 | Uchida et al. .................. | 502/51 |
| 4,880,886 A | * | 11/1989 | Kondo et al. .................. | 526/80 |
| 5,387,720 A | | 2/1995 | Neher et al. | |
| 5,677,261 A | | 10/1997 | Tenten et al. | |
| 5,959,143 A | | 9/1999 | Sugi et al. | |
| 6,403,829 B1 | | 6/2002 | Unverricht et al. | |
| 6,525,217 B1 | * | 2/2003 | Unverricht et al. .......... | 562/544 |
| 7,396,962 B1 | | 7/2008 | Dubois et al. | |
| 2003/0109381 A1 | | 6/2003 | Ohishi et al. | |

FOREIGN PATENT DOCUMENTS

| | | |
|---|---|---|
| CN | 1344756 A | 4/2002 |
| JP | 55-102536 A | 8/1980 |
| JP | 64-63543 A | 3/1989 |
| JP | 6-211724 A | 8/1994 |
| JP | 8-252464 A | 10/1996 |
| JP | 8-299797 A | 11/1996 |
| JP | 2001-79408 A | 3/2001 |
| JP | 2002-539103 A | 11/2002 |
| WO | WO 2004/069293 A1 | 8/2004 |

* cited by examiner

*Primary Examiner*—Paul A Zucker
*Assistant Examiner*—Yevegeny Valenrod

(57) ABSTRACT

There is provided a novel process for producing acrylic acid by which acrylic acid can be obtained from a raw material independent of petroleum. The process for producing acrylic acid according to the present invention comprises the steps of: applying a dehydration reaction to glycerol as a raw material in a gas phase; and then applying a gas phase oxidation reaction to a gaseous reaction product formed by the dehydration reaction.

9 Claims, No Drawings

METHOD FOR PRODUCING ACRYLIC ACID

TECHNICAL FIELD

The present invention relates to a novel process for producing acrylic acid by which acrylic acid can be obtained from a raw material independent of petroleum.

BACKGROUND ART

As processes for producing acrylic acid, from old times there have been known a process in which acetylene, carbon monoxide and water are made to react together in the presence of a nickel catalyst (so-called Reppe process) and a process in which acrylonitrile is hydrolyzed. However, thereafter, a process of two-step gas phase oxidation of propylene, namely, a process in which propylene is air-oxidized to convert it into acrolein and then this acrolein is further oxidized to convert it into acrylic acid, has been developed and now is industrially commonly employed (see, for example, JP-A-01-063543 (Kokai) and JP-A-55-102536 (Kokai)).

DISCLOSURE OF THE INVENTION

Object of the Invention

However, the conventional process of two-step gas phase oxidation of propylene uses petroleum-derived propylene as a raw material. Accordingly, in order to suppress global warming due to an increasing atmospheric level of $CO_2$ concentration and exhaustion of underground resources that are currently in progress, a process for producing acrylic acid from a raw material independent of petroleum is requested. Such a production process has, however, not yet been reported.

Thus, an object of the present invention is to provide a novel process for producing acrylic acid by which acrylic acid can be obtained from a raw material independent of petroleum.

SUMMARY OF THE INVENTION

The present inventors diligently studied to solve the above problems, and have consequently conceived a production of acrylic acid from glycerol as a raw material that is easily available from oils-and-fats existing in the animate nature. Then, the present inventors have completed the present invention by finding that acrylic acid can be obtained by applying a dehydration reaction to glycerol in a gas phase and then applying a gas phase oxidation reaction to a gaseous reaction product formed by the dehydration reaction.

That is, a process for producing acrylic acid according to the present invention is a process comprising the steps of: applying a dehydration reaction to glycerol as a raw material in a gas phase; and then applying a gas phase oxidation reaction to a gaseous reaction product formed by the dehydration reaction.

DETAILED DESCRIPTION OF THE INVENTION

Hereinafter, detailed descriptions are given about the process for producing acrylic acid according to the present invention. However, the scope of the present invention is not bound to these descriptions. And other than the following illustrations can also be carried out in the form of appropriate modifications of the following illustrations within the scope not departing from the spirit of the present invention.

The process for producing acrylic acid according to the present invention is a process comprising the steps of: applying a dehydration reaction to glycerol in a gas phase; and then applying a gas phase oxidation reaction to a gaseous reaction product formed by the dehydration reaction.

The present invention uses glycerol as a raw material. The glycerol to be subjected to the dehydration reaction as a raw material may be 100% pure glycerol, or may be an aqueous glycerol solution which is a mixture of glycerol and water. Glycerol and the aqueous glycerol solution are recovered in hydrolysis of various oils-and-fats or from waste fluids in soap production and are therefore industrially easily available. In addition, glycerol is expected to be generated in abundance as a by-product in production of a bio-diesel fuel as a renewable fuel by hydrolysis of vegetable oils in the future, and effective use thereof is desired. The present invention provides a process for producing acrylic acid as a useful chemical from glycerol which is such an easily available and renewable raw material, and this process is also a process for providing acrylic acid of which the source of carbon is carbon dioxide fixed by plants and which substantially does not lead to the increase of carbon dioxide in the air even when incinerated.

In the present invention, when the aqueous glycerol solution is used as a raw material, the water content of this aqueous glycerol solution is preferably not more than 50% by weight. When the water content of the aqueous glycerol solution as a raw material is more than 50% by weight, the aqueous glycerol solution needs much energy to vaporize and also enormous cost of wastewater treatment, and is therefore so disadvantageous economically as to hamper the industrial implementation of the process for producing acrylic acid of the present invention. The water content of the aqueous glycerol solution as a raw material is more preferably not more than 30% by weight, still more preferably not more than 20% by weight, and most preferably not more than 10% by weight.

The dehydration reaction in the present invention is a reaction of converting glycerol into acrolein and conducted by vaporizing the raw material (glycerol or aqueous glycerol solution) so as to be gaseous and then making this gas conduct a gas phase reaction in the presence of a catalyst. Examples of the catalyst that can be used in the aforementioned dehydration reaction include: natural and synthetic clay compounds such as kaolinite, bentonite, montmorillonite and zeolite; catalyst such that phosphoric acid or sulfuric acid is supported on a support such as alumina; inorganic oxides or inorganic composite oxides such as $Al_2O_3$, $TiO_2$, $ZrO_2$, $SnO_2$, $V_2O_5$, $SiO_2$—$Al_2O_3$, $SiO_2$—$TiO_2$ and $TiO_2$—$WO_3$; solid acidic substances such as sulfates, carbonates, nitrates and phosphates of metals such as $MgSO_4$, $Al_2(SO_4)_3$, $K_2SO_4$, $AlPO_4$, and $Zr_3(PO_4)_2$. It is usually preferable that these are used in the shape of such as sphere, pillar, ring, saddle. When the above-mentioned substance is a powder, it may be molded alone, or may be used in the form such as impregnated into a alreadymolded support or applied to its surface. The reaction temperature in the aforementioned dehydration reaction is preferably set in the range of 200 to 370° C., though not especially limited.

Specifically, for example, the aforementioned dehydration reaction may be conducted by vaporizing the raw material so as to be gaseous and then passing a flow of this gas through a reactor filled with the aforementioned catalyst and controlled to the aforementioned reaction temperature. The flow rate of the gas when being passed through the reactor is, for example, preferably controlled to a space velocity of 100 to 20000 $h^{-1}$, though not especially limited.

In addition, in the aforementioned dehydration reaction, it is preferable that: to the gas generated by the vaporization of the raw material, there is added an inert gas, and then a flow of the resultant mixed gas is passed through the reactor. Specifically, it is preferable that the concentration of the inert gas in the gas being supplied to the reactor of the aforementioned dehydration reaction is controlled to not less than 50% by volume. Incidentally, as the aforementioned inert gas, for example, it is possible to use such as nitrogen gas, carbon dioxide gas, rare gas, and water vapor.

The gas phase oxidation reaction in the present invention is a reaction of converting acrolein, formed by the aforementioned dehydration reaction, into acrylic acid and conducted by making a gaseous reaction product, formed by the aforementioned dehydration reaction, conduct a gas phase reaction in the presence of a catalyst. Examples of the catalyst that can be used in the aforementioned gas phase oxidation reaction include: solid catalysts including such as iron oxide, molybdenum oxide, titanium oxide, vanadium oxide, tungsten oxide, antimony oxide, tin oxide, copper oxide, and their mixtures and composite oxides. These may be used also in the form supported on supports (e.g. zirconia, silica, alumina and their composite oxides, and silicon carbide). The reaction temperature in the aforementioned gas phase oxidation reaction is preferably set in the range of 200 to 400° C., though not especially limited.

Specifically, for example, the aforementioned gas phase oxidation reaction may be conducted by passing a flow of the gas, formed by the aforementioned dehydration reaction, through a reactor filled with the aforementioned catalyst and controlled to the aforementioned reaction temperature. The flow rate of the gas when being passed through the reactor is, for example, preferably controlled to a space velocity of 100 to 2000 $h^{-1}$, though not especially limited.

In addition, in the aforementioned gas phase oxidation reaction, it is preferable that: when a flow of the gas, formed by the aforementioned dehydration reaction, is passed through the reactor, oxygen gas is beforehand added to that gas to increase the oxygen concentration. By this operation, the reactivity of the oxidation reaction is enhanced, so that acrylic acid can be obtained in a higher yield. Specifically, it is preferable that the oxygen concentration in the gas being supplied to the reactor of the aforementioned gas phase oxidation reaction is controlled to not less than 2% by volume. Incidentally, if the oxygen concentration in the gas being supplied to the reactor of the aforementioned gas phase oxidation reaction is too much high, then there occurs an unfavorable possibility that it may fall within the combustion range to thus involve risks of such as explosion. Therefore it is preferable that the upper limit value of the oxygen concentration is appropriately determined so as to avoid the combustion range in consideration of such as the concentration of unreacted raw glycerol, contained in the gas formed by the dehydration reaction, and the reaction temperature.

The process for producing acrylic acid of the present invention has only to be a process which comprises the steps of: applying the aforementioned dehydration reaction to the aforementioned raw material; and then applying the aforementioned gas phase oxidation reaction to a gaseous reaction product formed by the dehydration reaction. Thus, its specific working mode is not especially limited. For example, the following modes can be adopted: i) a mode that there is used a tandem-type reactor comprising two reaction tubes linked to each other, where the two reaction tubes are filled with a catalyst for the dehydration reaction and a catalyst for the gas phase oxidation reaction respectively and where the dehydration reaction and the gas phase oxidation reaction are separately conducted in their respective reaction tubes; ii) a mode that there is used a single-type reactor comprising one reaction tube, where the reaction tube is filled with a catalyst for the gas phase oxidation on the reaction gas outlet side and with a catalyst for the dehydration reaction of glycerol on the reaction gas inlet side, thus conducting in the one reaction tube the dehydration reaction followed by the gas phase oxidation reaction; and iii) a mode that there is used a single-type reactor comprising one reaction tube, where the one reaction tube is filled with catalysts for the dehydration reaction and for the gas phase oxidation reaction uniformly mixed together or with a catalyst which functions both for the dehydration reaction and the gas phase oxidation reaction, thus conducting the dehydration reaction and the gas phase oxidation reaction in the one reaction tube at the same time.

The aforementioned mode of conducting the dehydration reaction and the gas phase oxidation reaction in the tandem-type reactor (the aforementioned i)) has an advantage that the reaction temperatures of those reactions can be individually controlled within their respective optimum ranges, although there is an unfavorable possibility that the reaction product may crystallize in the joint of the reaction tubes to thus cause clogging. Moreover, in the tandem-type reactor, since a gas can be added through the joint, there is an advantage that oxygen can be added into a gas transferring from the aforementioned dehydration reaction to the aforementioned gas phase oxidation reaction, so it is possible to take the aforementioned mode of increasing the oxygen concentration in the gas which is to be subjected to the aforementioned gas phase oxidation reaction. Accordingly, in the aforementioned mode of conducting the dehydration reaction and the gas phase oxidation reaction in the tandem-type reactor, it is preferable to add oxygen into the gas transferring from the aforementioned dehydration reaction to the aforementioned gas phase oxidation reaction.

The aforementioned modes of conducting the dehydration reaction and the gas phase oxidation reaction in the single-type reactor (the aforementioned ii) and iii)) have an advantage of enabling a compact system, although it is impossible to take the aforementioned mode of increasing the oxygen concentration in the gas which is to be subjected to the aforementioned gas phase oxidation reaction or although there is a disadvantage in the maintenance aspect such as when only either one of the catalytic functions for the dehydration reaction and for the gas phase oxidation reaction is deteriorated, so that it becomes necessary to replace the deteriorated catalyst. In addition, particularly, the aforementioned mode ii) has a further advantage that if necessary, conducting the dehydration reaction and the gas phase oxidation reaction at different reaction temperatures becomes possible, for example, by dividing a heat medium circulating part of a multitubular reactor into two parts and circulating heat media of different temperatures. Furthermore, in the aforementioned mode ii), by filling an inert support between the catalyst for the gas phase oxidation and the catalyst for the dehydration reaction, it is possible that mutual contaminations of the catalyst for the gas phase oxidation and the catalyst for the dehydration reaction are prevented, or that a catalytic reaction at an improper reaction temperature is suppressed. As the inert support, low surface area heat-resistant materials, for example, metal fillers (e.g. stainless Raschig rings) and ceramic sinters, can be used.

Incidentally, acrylic acid produced by the production process of the present invention can be industrially further subjected to publicly known purification methods (for example, processed by steps such as a step of collecting acrylic acid as a solution by using water or a solvent, a distillation step for removing low- and high-boiling-point materials from the resultant solution containing acrylic acid, or a crystallization step for purifying acrylic acid by crystallizing it) to thus provide acrylic acid as a product. Then, this product can be used to produce, for example, polyacrylic acids (salts) as water-soluble polymers or water-absorbent resins, by publicly known polymerization methods such as thermal polymerization methods and photopolymerization methods.

According to the present invention, acrylic acid can be obtained from glycerol which is a raw material independent of petroleum. Further, according to the present invention, glycerol, which is a by-product in hydrolysis of vegetable oils for such as production of a bio-diesel fuel and in soap production, can be effectively used as a raw material. Moreover, glycerol derived from vegetable oils is such that its carbon is derived from carbon dioxide in the air. Therefore, even if acrylic acid produced by the present invention and products therefrom are finally incinerated, it does not lead to the increase of carbon dioxide in the air, and thus there is also an effect of preventing global warming. Besides, there is no worry of exhaustion of resources such as fossil resources, because vegetable oils are renewable resources.

DETAILED DESCRIPTION OF THE PREFERRED EMBODIMENTS

Hereinafter, the present invention is more specifically illustrated by the following Examples of some preferred embodiments in comparison with Comparative Examples not according to the present invention. However, the present invention is not limited to them. Hereinafter, unless otherwise noted, the unit "% by mol" is referred to as "%".

PRODUCTION EXAMPLE 1

Production of Catalyst (A1)

An amount of 194 g of a support in a spherical shape of 7 to 10 mm comprising α-alumina as the main component was impregnated with 4 g of phosphoric acid and 2 g of silica sol and then dried at 80° C. in a rotary evaporator to obtain a catalyst (A1) of 2% by weight in supporting ratio of phosphoric acid.

PRODUCTION EXAMPLE 2

Production of Catalyst (A2)

Firstly, while 500 mL of water was heated at 90° C. and stirred, into this there were added 63 g of ammonium paramolybdate, 19.2 g of ammonium metavanadate and 8.0 g of ammonium paratungstate to dissolve them. Furthermore, an aqueous copper nitrate solution, which had been previously prepared by dissolving 15.8 g of copper nitrate into 50 mL of water, was added to prepare a chemical liquid. Into a porcelain evaporating dish as set on a water bath of 90° C., there was placed 200 g of a support in a spherical shape of 6 to 8 mm comprising α-alumina as the main component, and then there was poured the aforementioned chemical liquid to support it thereon under stirring, thus obtaining a catalyst precursor. Next, this catalyst precursor was calcined for 6 hours at 400° C. to obtain a catalyst (A2) of 31% by weight in supporting ratio of an Mo—V—W—Cu-composite oxide.

PRODUCTION EXAMPLE 3

Production of catalyst (B1)

An amount of 188 g of a support in a spherical shape of 3 to 5 mm comprising α-alumina as the main component was impregnated with 10 g of phosphoric acid and 2 g of silica sol and then dried at 80° C. in a rotary evaporator to obtain a catalyst (B1) of 5% by weight in supporting ratio of phosphoric acid.

PRODUCTION EXAMPLE 4

Production of Catakyst (B2)

Firstly, while 500 mL of water was heated at 90° C. and stirred, into this there were added 70 g of ammonium paramolybdate, 21.3 g of ammonium metavanadate and 8.9 g of ammonium paratungstate to dissolve them. Furthermore, an aqueous copper nitrate solution, which had been previously prepared by dissolving 17.6 g of copper nitrate into 150 mL of water, was added to prepare a chemical liquid. Into a porcelain evaporating dish as set on a water bath of 90° C., there was placed 200 g of a support in a spherical shape of 3 to 5 mm comprising α-alumina as the main component, and then there was poured the aforementioned chemical liquid to support it thereon under stirring, thus obtaining a catalyst precursor. Next, this catalyst precursor was calcined for 6 hours at 400° C. to obtain a catalyst (B2) of 35% by weight in supporting ratio of an Mo—V—W—Cu-composite oxide.

PRODUCTION EXAMPLE 5

Prodcution of Catalyst (C)

An amount of 177 g of a support in a spherical shape of 3 to 5 mm comprising α-alumina as the main component was impregnated with 20 g of phosphoric acid and 3 g of silica sol and then dried at 80° C. in a rotary evaporator to obtain a catalyst (C') of 10% by weight in supporting ratio of phosphoric acid.

Next, while 500 mL of water was heated at 90° C. and stirred, into this there were added 70 g of ammonium paramolybdate, 21.3 g of ammonium metavanadate and 8.9 g of ammonium paratungstate to dissolve them. Furthermore, an aqueous copper nitrate solution, which had been previously prepared by dissolving 17.6 g of copper nitrate into 150 mL of water, was added to prepare a chemical liquid. This chemical liquid was sprayed onto the surface of the aforementioned catalyst (C') uniformly with a spray nozzle so that the chemical liquid component would be supported only on the outer portion of the catalyst, thus obtaining a catalyst precursor. Next, this catalyst precursor was calcined for 6 hours at 400° C. to obtain a catalyst (C) of 32% by weight in supporting ratio of an Mo—V—W—Cu-composite oxide.

EXAMPLE 1

A tandem-type reactor comprising two reaction tubes linked to each other (both were made of SUS and had a diameter of 25 mm) was used. The first-step reaction tube was filled with 50 mL of catalyst (A1), and the second-step reaction tube was filled with 50 mL of catalyst (A2). Then, those reaction tubes were placed into molten salt baths of variable temperatures, and the molten salt temperatures were set to be 295° C. for the first step and 275° C. for the second step.

An aqueous glycerol solution having a water content of 15% by weight was vaporized, and an oxygen-containing gas was added thereto. A flow of the resultant mixed gas (gas composition: glycerol 10% by volume, water 9% by volume, oxygen 6% by volume and nitrogen 75% by volume) was passed through the aforementioned first-step reaction tube and the aforementioned second-step reaction tube in sequence at a flow rate of 420 mL/min, and then the discharged gas was collected with a collecting bottle containing water to obtain acrylic acid. Its yield was 55%.

EXAMPLE 2

A tandem-type reactor comprising two reaction tubes linked to each other (both were made of SUS and had a diameter of 25 mm) was used. The first-step reaction tube was filled with 35 mL of catalyst (B1), and the second-step reaction tube was filled with 50 mL of catalyst (B2). Then, those reaction tubes were placed into molten salt baths of variable temperatures, and the molten salt temperatures were set to be 290° C. for the first step and 270° C. for the second step.

An aqueous glycerol solution having a water content of 9% by weight was vaporized, and nitrogen gas was added thereto. A flow of the resultant mixed gas (gas composition: glycerol 14% by volume, water 7% by volume and nitrogen 79% by volume) was passed through the aforementioned first-step reaction tube at a flow rate of 294 mL/min, and then into a gas flow having passed through the first-step reaction tube, there was added and mixed air at a flow rate of 126 mL/min, and then a flow of the resultant mixed gas was passed through the aforementioned second-step reaction tube, and then the discharged gas was collected with a collecting bottle containing water to obtain acrylic acid. Its yield was 63%.

EXAMPLE 3

A single-type reactor comprising one reaction tube (made of SUS and having a diameter of 25 mm) was used. This reaction tube was filled with 50 mL of catalyst (B1), 10 mL of stainless Raschig rings, and 50 mL of catalyst (B2) in this order. The part filled with the catalyst (B1) was used as a first-step reaction zone, and the part filled with the catalyst (B2) was used as a second-step reaction zone. Then, the aforementioned reaction tube was placed into a molten salt bath which was segmented by a shield and was temperature-variable in each segment, wherein the shield was positioned so as to correspond to the filled position of the stainless Raschig rings in the reaction tube so that the first-step reaction zone and the second-step reaction zone could be independently controlled to their respective temperatures. The molten salt temperatures were set to be 292° C. for the first step and 270° C. for the second step.

An aqueous glycerol solution having a water content of 8% by weight was vaporized, and an oxygen-containing gas was added thereto. A flow of the resultant mixed gas (gas composition: glycerol 10% by volume, water 4% by volume, oxygen 6% by volume and nitrogen 80% by volume) was passed through the aforementioned reaction tube at a flow rate of 420 mL/min, and then the discharged gas was collected with a collecting bottle containing water to obtain acrylic acid. Its yield was 65%.

EXAMPLE 4

A single-type reactor comprising one reaction tube (made of SUS and having a diameter of 25 mm) was used. This reaction tube was filled with 70 mL of catalyst (B1) and 30 mL of catalyst (B2) having been uniformly mixed together. Then, the aforementioned reaction tube was placed into a molten salt bath of variable temperature, and the molten salt temperature was set to be 295° C.

An aqueous glycerol solution having a water content of 2% by weight was vaporized, and an oxygen-containing gas was added thereto. A flow of the resultant mixed gas (gas composition: glycerol 10% by volume, water 1% by volume, oxygen 6% by volume and nitrogen 83% by volume) was passed through the aforementioned reaction tube at a flow rate of 420 mL/min, and then the discharged gas was collected with a collecting bottle containing water to obtain acrylic acid. Its yield was 57%.

EXAMPLE 5

A single-type reactor comprising one reaction tube (made of SUS and having a diameter of 25 mm) was used. This reaction tube was filled with 50 mL of catalyst (C). Then, the aforementioned reaction tube was placed into a molten salt bath of variable temperature, and the molten salt temperature was set to be 294° C.

An aqueous glycerol solution having a water content of 9% by weight was vaporized, and an oxygen-containing gas was added thereto. A flow of the resultant mixed gas (gas composition: glycerol 10% by volume, water 5% by volume, oxygen 6% by volume and nitrogen 79% by volume) was passed through the aforementioned reaction tube at a flow rate of 420 mL/min, and then the discharged gas was collected with a collecting bottle containing water to obtain acrylic acid. Its yield was 58%.

INDUSTRIAL APPLICATION

The process for producing acrylic acid according to the present invention is a novel process by which acrylic acid can be obtained from a raw material independent of petroleum, and is useful as a next-generation process for producing acrylic acid. In addition, even if acrylic acid produced by the process for producing acrylic acid according to the present invention, and products therefrom, are finally incinerated, it does not lead to the increase of carbon dioxide in the air, and thus there is also an effect of preventing global warming.

The invention claimed is:

1. A process for producing acrylic acid, comprising the steps of:
   a) vaporizing a raw material comprising an aqueous glycerol solution to generate a first gas, wherein said aqueous glycerol solution has a water content, of not more than 20% by weight;
   b) applying a dehydration reaction to glycerol in a gas phase that includes said first gas; and
   c) applying a gas phase oxidation reaction to a gaseous reaction product formed by the dehydration reaction to obtain said acrylic acid; and
   d) conducting the dehydration reaction and the gas phase oxidation reaction in a single-type reactor comprising one reaction tube, where said one reaction tube is filled with catalysts for the dehydration reaction and for the gas phase oxidation reaction uniformly mixed together or with a catalyst which functions both for the dehydration reaction and the gas phase oxidation reaction, thus conducting the dehydration reaction and the gas phase oxidation reaction in said one reaction tube at the same time.

2. The process for producing acrylic acid according to claim 1, and further comprising the steps of:
   a) adding an inert gas to the first gas to obtain a resultant mixed gas, wherein the inert gas is selected from the group consisting of nitrogen gas, carbon dioxide gas and rare gas; and
   b) controlling a concentration of said inert gas in said resultant mixed gas to a concentration of not less than 50% by volume.

3. The process for producing acrylic acid according to claim 1, wherein the gas phase in which the dehydration reaction is conducted is a mixed gas comprising glycerol, water vapor and oxygen.

4. The process for producing acrylic acid according to claim 3, wherein the amount of the water vapor relative to the glycerol in the mixed gas is not larger than 1.2 times by mol.

5. The process for producing acrylic acid according to claim 1, wherein the acrylic acid is used to produce a water-absorbent resin.

6. The process for producing acrylic acid according to claim 1, further comprising the step of collecting the resultant acrylic acid as a solution by using water or a solvent.

7. The process for producing acrylic acid according to claim 6, further comprising a distillation step for removing low- and high-boiling-point materials from the resultant solution containing acrylic acid.

8. The process for producing acrylic acid according to claim 6, further comprising a crystallization step for purifying acrylic acid by crystallizing it.

9. A petroleum independent process for producing acrylic acid, comprising the steps of:
   a) obtaining glycerol from one of i) hydrolysis of oils-and-fats, ii) waste fluids in soap production, and iii) a by-product in production of a bio-diesel fuel as a renewable fuel;
   b) vaporizing a raw material comprising an aqueous glycerol solution having said glycerol to generate a first gas, wherein said aqueous glycerol solution has a water content of not more than 20% by weight;
   c) adding an inert gas to the first gas to obtain a resultant mixed gas, wherein the inert gas is selected from the group consisting of nitrogen gas, carbon dioxide gas and rare gas, and controlling a concentration of said inert gas in said resultant mixed gas to a concentration of not less than 50% by volume;
   d) applying a dehydration reaction to glycerol in a gas phase that includes said resultant mixed gas, wherein the gas phase in which said dehydration reaction is conducted comprises glycerol, water vapor and oxygen, and wherein the amount of the water vapor relative to the glycerol in the mixed gas is not larger than 1.2 times by mol;
   e) applying a gas phase oxidation reaction to a gaseous reaction product formed by the dehydration reaction to obtain said acrylic acid; and
   f) conducting the dehydration reaction and the gas phase oxidation reaction in a single-type reactor comprising one reaction tube, where said one reaction tube is filled with catalysts for the dehydration reaction and for the gas phase oxidation reaction uniformly mixed together or with a catalyst which functions both for the dehydration reaction and the gas phase oxidation reaction, thus conducting the dehydration reaction and the gas phase oxidation reaction in said one reaction tube at the same time.

* * * * *